United States Patent [19]
Tsuchida et al.

[11] 4,452,890
[45] Jun. 5, 1984

[54] METHOD OF PRODUCING L-THREONINE BY FERMENTATION

[75] Inventors: Takayasu Tsuchida, Yokohama; Kiyoshi Miwa, Matsudo; Shigeru Nakamori, Yokohama, all of Japan

[73] Assignee: Ajinomoto Company Incorporated, Tokyo, Japan

[21] Appl. No.: 376,396

[22] Filed: May 10, 1982

[30] Foreign Application Priority Data

May 11, 1981 [JP] Japan .................................. 56-70383

[51] Int. Cl.³ ....................... C12P 13/08; C12N 15/00
[52] U.S. Cl. .................................. 435/115; 435/172.3; 935/61; 935/72
[58] Field of Search ................................ 435/115, 172

[56] References Cited

U.S. PATENT DOCUMENTS 3,732,144  5/1973  Nakayama et al. ................. 435/115
4,347,318  8/1982  Miwa et al. .......................... 435/115

*Primary Examiner*—Alvin E. Tanenholtz
*Attorney, Agent, or Firm*—Oblon, Fisher, Spivak, McClelland & Maier

[57] ABSTRACT

An L-threonine microorganism is produced by inserting a restriction endonuclease fragment of chromosomal DNA controlling α-amino-β-hydroxy valeric acid resistance from a Brevibacterium or Corynebacterium into a plasmid and transforming a Brevibacterium or Corynebacterium which is sensitive to α-amino-β-hydroxy valeric acid.

10 Claims, No Drawings

METHOD OF PRODUCING L-THREONINE BY FERMENTATION

BACKGROUND OF THE INVENTION

1. Field of the Invention

The present invention relates to a method for producing L-threonine by fermentation, and particularly relates to a method for producing L-threonine with a microorganism of the genus Brevibacterium and Corynebacterium constructed by a gene recombination technique.

2. Description of the Prior Art

Hitherto, in order to render a wild strain capable of producing L-threonine from carbohydrates, it has been necessary to induce artificial mutants form the wild strain. There are many known L-threonine-producing artificial mutants. Most of the known threonine-producing mutants are resistant to α-amino-β-hydroxy valeric acid (hereinafter referred to as "AHV"), and belong to the genus Brevibacterium or Corynebacterium. These microorganisms produce L-threonine in a yield of from 10 to 20%.

Examples of publications are U.S. Pat. No. 3,582,471, U.S. Pat. No. 3,580,810 and Japanese Publication No. 47-34956, in which threonine producing mutants resistant to AHV and belonging to the genera Brevibacterium, Escherichia and Corynebacterium are disclosed, respectively. Recent publications concering threonine production especially by mutant of the genera Brevibacterium and Corynebacterium are Japanese Published Unexamined Patent Application Nos. 51-54984, 53-101591, 54-32693, 54-35285, 54-35286, 54-35288, 54-37886 and 54-92692.

Another approach to increase the productivity of threonine in microorganism is found in U.S. Pat. No. 4,278,765 and Japanese Published Unexamined Patent Applications Nos. 55-131397 and 56-15696, in which threonine producing *Escherichia coli* strains transformed with a recombinant plasmid DNA and then constructed by a gene-recombination technique were disclosed.

However, it has been difficult to construct commercially applicable threonine-producer of *Escherichia coli* by the gene-recombination technique, because originally Escherichia strains can not express high productivity of L-threonine and then recombinant strains derived from such Escherichia strains can not produce high amount of L-threonine.

On the other hand, threre are many strains in the genera Brevibacterium and Corynebacterium which produce high amount of L-threonine, and therefore the strains of Corynebacterium and Brevibacterium may be suitable as the original strain for construction of L-threonine-producer by gene-recombination technique. However, although presence of plasmids in the strains of Brevibacterium and Corynebacterium is known (Publication of European Patent Application No. 0030391), the plasmids have no specific characteristics to be used as the marker for identification of the plasmids, and therefore it has been very difficult to select recombinant plasmids, derived from the plasmids of Brevibacterium and Corynebacterium. For the reason as above, it has been difficult to construct L-threonine-producer from the L-threonine producing Brevibacterium and Corynebacterium by gene-recombination technique.

A need therefore, continues to exist for development of novel process for production of L-threonine in high yields.

SUMMARY OF THE INVENTION

It is therefore an object of the present invention to provide for a novel method for producing L-threonine by fermentation in high yields.

The inventors have found that strains of the genus Brevibacterium or Corynebacterium transformed to L-threonine-producer can be isolated by selecting strains transformed to become resistant to AHV.

It is now provided a method for producing L-threonine by fermentation which comprises aerobically culturing in an aqueous culture medium an L-threonine producing microorganism obtained by isolating a strain transformed to become resistant to AHV after incorporation into a recipient strain of the genus Brevibacterium or Corynebacterium which is sensitive to AHV, of a plasmid DNA obtained from a microorganism of the genus Brevibacterium or Corynebacterium and having been inserted therein a fragment of chromosomal DNA derived from a DNA-donor strain of the genus Brevibacterium or Corynebacterium which is resistant to AHV, and recovering L-threonine accumulated in the resulted culture liquid.

The present invention also provides a method for constructing an L-threonine producing strain which comprises:

(a) separating a plasmid DNA from a microorganisms of the genus Brevibacterium and Corynebacterium, (b) inserting into the plasmid DNA a fragment of chromosomal DNA derived from a DNA-donor strain of the genus Brevibacterium and Corynebacterium resistant to AHV to obtain a recombinant plasmid DNA (c) incorporating the recombinant plasmid DNA into a recipient strain of the genes Brevibacterium or Corynebacterium which is sensitive to AHV, and (d) isolating a strain transformed to become resistant to AHV.

DETAILED DESCRIPTION OF THE PREFERRED EMBODIMENTS

The DNA-donor strain used to construct the L-threonine producer of this invention is a mutant of the genus Brevibacterium or Corynebacterium resistant to AHV. Strains having higher productivity of L-threonine are used preferably as the DNA-donor. The mutant resistant to AHV used as the DNA-donor can be obtained by conventional mutation techniques such as exposing the parent strain to 250 μg/ml of N-methyl-N'-nitro-N-nitrosoguanidine in a buffer solution and separating the colony which appeared to the agar medium containing an amount of AHV inhibitive to the growth of the parent strain. Such DNA-donor naturally has a chromosomal DNA region controlling AHV resistance.

Known strains resistant to AHV are, for example, mutant of Brevibacterium resistant to AHV (Japanese Published Examined Patent Application 26708/1970, mutant of Corynebacterium resistant to AHV (Japanese Published Examined Patent Application 34956/1972), mutant of Brevibacterium resistant to AHV and requiring L-lysine, L-methonine or L-isoleucine (Japanese Published Examined Patent Application 44876/1973), mutant of Brevibacterium resistant to AHV and decoyinine or psicofuranine (Japanese Published Unexamined Patent Application No. 32693/1979), mutant of Brevibacterium resistant to AHV and α-chlorocaprolactam, γ-methyllysine or γ-carbobenzoxylysine (Japanese Published Unexamined Patent Application No. 35285/1979), mutant of Brevibacterium resistant to AHV and requiring alanine (Japanese Published Unexamined Patent Application No. 35286/1979), mutant of Brevibacterium resistant to AHV and S-methylcysteinesulfoxide, S-methylglycinesulfoxide, carbobenzoxyvaline, carbobenzoxythreonine or N-benzoylallothreonine (Japanese Published Unexamined Patent Application No. 35288/1979), mutant of Brevibacterium resistant to AHV and p-chloro-m-fluoromethyl phenylalanine (Japanese Published Unexamined Patent Application No. 37886/1979) and mutant of Brevibacterium resistant to AHV and leucine-analogue (Japanese Published Unexamined Patent Application No. 92692/1979).

Other than the DNA-donors listed above, AHV-resistant strains can be obtained by giving AHV-resistant by a conventional manner to so cold Coryne-form glutamic acid producing bacteria, of which typical strains are shown below:

Brevibacterium divaricatum ATCC 14020
Brevibacterium saccharoliticum ATCC 14066
Brevibacterium immariophilum ATCC 14068
Brevibacterium lactofermentum ATCC 13869
Brevibacterium roseum ATCC 13825
Brevibacterium flavum ATCC 13826
Brevibacterium thiogenitalis ATCC 19240
Corynebacterium acetoacidophilum ATCC 13870
Corynebacterium acetoglutamicum ATCC 15806
Corynebacterium callunae ATCC 15991
Corynebacterium glutamicum ATCC 13032
Corynebacterium lilium ATCC 15990
Corynebacterium melassecola ATCC 17965

As the vector DNA, plasmids obtained from the Coryne-form glutamic acid producing bacteria of the genera Brevibacterium and Corynebacterium or their mutants, and derivatives of the plasmids can be used. Specimens of the plasmids are pAM 286 and pAM 330, and pHM 1519.

DNA-recipient used in the present invention are strains sensitive to AHV and belonging to the Coryne-form glutamic acid producing bacteria of the genera Brevibacterium and Corynebacterium. Especially, when a mutant sensitive to AHV which requires L-threonine is used as the DNA-recipient, it is more convenient to distinguish the threonine-producing transformant from the recipient, although the threonine-producing transformant can be distinguished from the recipient by AHV-resistance.

Chromosomal DNA is extracted from the DNA donor in a well known manner and treated with a restriction endonuclease by a well known method (Biochem. Biophys. Acta 383: 457 (1975)).

The vector DNA is also treated with a restriction endonuclease in an analogous manner. Various kinds of restriction endonucleases can be used, if the digestion of the chromosomal DNA is done partially. Thereafter, the digested chromosomal DNA and vector DNA are subjected to to a ligation reaction.

Recombination of DNA to prepare the recombinant plasmid can be carried out by the ligation reaction with a ligase, or by incorporating with terminal transferase deoxyadenylic acid and thymidylic acid, or deoxyguanylic acid and deoxycytidylic acid into the chromosomal DNA fragment and cleaved vector DNA and by subjecting the modified chromosomal DNA fragment and cleaved DNA to an annealing reaction.

The recombinant DNA thus obtained can be incorporated into the DNA-recipient by treating the cell of the DNA-recipient with calcium chloride to increase the permeability as is reported regarding E. coli K-12 (Mandel, M. and Higa, A., J. Mol. Biol., 53, 159 (1970)), or by applying for the incorporation cells of the DNA-recipient at a specific stage of growth when cells become capable of incorporating plasmids (competent cell) as is reported in Bacillus subtilis (Duncan, C. H., Wilson, G. A. and Young, F. E., Gene 1, 153 (1977)). The recombinant DNA can also be incorporated into the DNA-recipient by forming protoplast or spheroplast of the DNA-recipient which easily incorporates plasmid DNA as is known in Bacillus subtilis, actinomycetes and yeast (Chang, S and Choen, S. N., Molec, Gen. Genet, 168, 111 (1979)) Bibb, M. J. Ward, J. M. and Hopwood, O. A., Nature, 274, 398 (1978); Hinnen, A., Hicks, J. B. and Fink, G. R., Proc. Natl, Acad. Sci., U.S.A., 75, 1929 (1978)).

The desired transformant can be obtained by isolating the colonies appeared on a medium containing an amount of AHV inhibitive to the growth of the DNA-recipient. Threonine-producers can be obtained from the isolated colonies in high frequency.

The methods of culturing the L-threonine producing strains thus obtained are conventional, and are similar to the methods for the cultivation of known L-threonine producing microorganisms. Thus, the culture medium employed is a conventional one containing carbon sources, nitrogen sources, inorganic ions and, when required, minor organic nutrients such as vitamins or amino acids. Examples of suitable carbon sources include glucose, sucrose, lactose, starch hydrolysate and molasses. Gaseous ammonia, aqueous ammonia and ammonium salts and other nitrogen containing materials can be used as the nitrogen source.

Cultivation of the recombinant microorganisms is conducted under aerobic conditions in which the pH and the temperature of the medium are adjusted to a suitable level and continued until the formation of L-threonine ceases.

The L-threonine accumulated in the culture medium can be recovered by conventional procedures.

By the method of the present invention, L-threonine can be produced in higher yields than has been achieved in previously known methods using artificial mutants of Brevibacterium and Corynebacterium.

Having generally described this invention, a further understanding can be obtained by reference to certain specific examples which are provided herein for purposes of illustration only and are not intended to be limiting unless otherwise specified.

EXAMPLE 1

(1) Extration of DNA

Corynebacterium glutamicum AJ 11560 (FERM-P 5485) was exposed to 250 μg/ml N-methyl-N'-nitro-N-nitrosoguanidine in 1/10 M phosphate buffer of pH 7.2 at 30° C. for 30 minutes and colonies appeared on a minimum medium (M medium) (containing, per liter, 20 g glucose, 10 g ammonium sulfate, 2.5 g urea, 1 g $KH_2PO_4$, 0.4 g $MgSO_4.7H_2O$, 50 μg biotin, 200 μg thiamine.HCl, 0.01 g $FeSO_4$, 0.01 g $MnSO_4.4H_2O$, 1 g AHV and 2 g agar (pH 7.0)) were isolated as the AHV-resistant strains.

One of the AHV-resistant strains, No. 60 (NRRL B-15046) was cultured at 37° C. for 3 hours with shaking in 1 l of CMG-medium containing 1 g/dl peptone, 1 g/dl yeast extract, 0.5 g/dl glucose and 0.5 g/dl NaCl (pH was adjusted to 7.2), and bacterial cells in the exponential growth phase were harvested. Chromosomal DNA was extracted by a conventional phenol-method, and 0.6 mg of purified DNA was obtained.

Corynebacterium glutamicum AJ 11560 was newly isolated as a suitable strain for the purpose of this invention. This strain was classified to the section III of the genus Corynebacterium described in Bergey's Manual of Determinative Bacteriology (8th edition, 1974). However, taxonomic characteristics of the species belonging to section III are not disclosed in the Manual, but only disclosed the name of species of section III. Therefore, all original reports disclosed in the Manual as to section III are referred to. AJ 11560 was identified with Corynebacterium glutamicum described in Bull. Agr. Chem. Soc. Japan 22, 176–185 (1958) and J. Gen. Appl. Microbiol., 13, 279–301 (1967).

(2) Preparation of vector DNA

As the vector, DNA of pAM 286, a plasmid of Corynebacterium glutamicum was prepared as follows:

Corynebacterium glutamicum AJ 11560 harboring the plasmid pAM 286 was incubated at 30° C. in 1 l of CMG medium until the late log phase, cells were harvested and then lysed by treatment with lysozyme and SDS. The lysate was centrifuged at 30,000×g for 30 minutes to obtain the supernatant. After concentrating the supernatant, 60 μg of pAM 286 plasmid DNA was obtained by fractionation using agarose gel electrophotoresis.

(3) Insertion of chromosomal DNA fragment into vector

10 μg of the chromosomal DNA was treated with the restriction endonuclease XbaI at 37° C. for 10, 30 and 60 minutes, respectively, to cleave the DNA chains, and then heated at 65° C. for 5 minutes, respectively. 5 μg of the vector DNA was also treated with the restriction endonuclease XbaI at 37° C. for 60 minutes to cleave the DNA completely, and then heated at 65° C. for 5 minutes.

The digested chromosomal DNA solution and cleaved vector DNA solution were mixed and subjected to the ligation reaction of DNA fragments by a T4 phase DNA-ligase in the presence of ATP and dithiothreitol at 10° C. for 24 hours. The reaction mixture was then heated at 65° C. for 5 minutes, and two folds volume of ethanol was added to it. The precipitated recombinant DNA was recovered.

(4) Genetic transformation with recombinant plasmid

A histidine requiring strain, No. 200 (NRRL B-15047) which was derived from Corynebacterium glutamicum AJ 11560 by N-methyl-N'-nitro-N-nitrosoguanidine mutagenesis, (250 μg/ml in a 1/10 M phosphate buffer, pH 6.0 at 30° C. for 60 minutes, and isolated as the histidine requiring mutant) was cultured in 20 ml of CMG medium at 30° C. with shaking. Cells in exponential growth phase were harvested, and "competent" cells having the ability of DNA uptake were prepared by calcium chloride method. The calcium chloride method was conformed to that disclosed in Mandel, M and Higa, A., J. Mol. Biol., 53, 159 (1970). That is, No. 200 was inoculated into 20 ml CMG medium and cultured until the cell density reached 0.6 A650/ml. Cells were harvested, suspended in ice-cooled 0.1 M MgCl2, collected, suspended in 5 ml of 0.1 M CaCl2 with ice-cooling, and held at 0° C. for 20 minutes with shaking occasionally. The cells were separated from the suspension suspended again in a small amount of 0.1 M CaCl2 and then obtained the competent cells suspension. Into the competent cell suspension, a solution of DNA obtained in step (3) was added to introduced the DNA into the cell. The reaction mixture was spread on the plate of M-medium supplemented with 0.1 g/l L-histidine.

Colonies appeared on the plate after incubation at 37° C. for 4 days and transformed to become AHV-resistant were picked up and L-threonine-producine transformants were selected.

Thus, AJ 11682 (FERM-P 5973=FERM-BP118) was obtained as the best threonine producing transformant.

(5) Production of L-threonine

L-Threonine productivity of AJ 11682 obtained in step (4) was tested comparing with the DNA-donor and DNA-recipient. The results are shown in Table 1.

The fermentation medium contained 10 g/dl glucose, 3 g/dl ammonium sulfate, 0.1 g KH2PO4, 0.04 g/dl MgSO4.7H2O, 2 mg/dl soyprotein hydrolysate ("MIEKI"), 10 μg/dl thiamine.HCl, 50 μg/dl biotin, 1 mg/dl FeSO4.7H2O, 1 mg/dl MnSO4.4H2O 10 mg/dl L-histidine and 5 g/dl CaCO3 (separately sterilized) and the pH was adjusted to 7.2.

Twenty ml batches of the fermentation medium were placed in 500 ml flasks, inoculated with one loopful inoculum of the test microorganism, and the cultivation was carried out at 37° C. for 72 hours.

The amount of L-threonine in the supernatant of the fermentation broth was determined by microbiological assay.

TABLE 1

| Microorganism tested | L-threonine produced (mg/dl) |
|---|---|
| No. 60 | 140 |
| No. 200 | 0 |
| AJ 11682 | 295 |

EXAMPLE 2

(1) Extraction of DNA

In the method shown in step(1) of Example 1, 2.1 mg of chromosomal DNA was obtained from a AHV resistant mutant, No. 107 (NRRL B-15048) which had been derived from Brevibacterium lactofermentum ATCC 13869.

(2) Preparation of vector DNA

In the method shown in step(2) of Example 1, 132 μg of a plasmid pAM 330 was separated from Brevibacterium lactofermentum ATCC 13869 as the vector DNA.

(3) Insersion of chromosomal DNA fragment into vector

Ten μg of chromosomal DNA obtained in step(3) was digested by the manner shown in step(3) of Example 1. The vector DNA was also cut by the manner shown in step(3), and the digested chromosomal DNA and the cutted vector DNA were subjected to the ligation reaction shown in step(3) of Example 1.

(4) Genetic transformation with the recombinant plasmid

From *Brevibacterium lactofermentum* ATCC 13869. No. S-18 (NRRL B-15049) which is resistant to streptomycine and requires L-histidine was induced as the DNA-recipient by the method shown in step(4) of Example 1, A transformant, AJ 11683 (FERM-P 5974=FERM-BP119) resistant to AHV and capable of producing L-threonine was obtained using the DNA-recipient.

(5) Production of L-threonine

The transformant AJ 11683 obtained in step(4) was tested its productivity of L-threonine by the method in step(5) of Example 1. The results are shown in Table 2.

TABLE 2

| Microorganism tested | L-threonine produced (mg/dl) |
|---|---|
| No. 107 | 51 |
| No. S-18 | 0 |
| AJ 11683 | 132 |

What is claimed as new and intended to be covered by Letters Patent of the United States is:

1. A method for producing L-threonine by fermentation which comprises aerobically culturing in an aqueous culture medium an L-threonine producing microorganism obtained by isolating a strain transformed to become resistant to α-amino-β-hydroxy-valeric acid after incorporation into a recipient strain of the genus Brevibacterium or Corynebacterium which is sensitive to α-amino-β-hydroxy valeric acid, of a plasmid DNA obtained from a microorganism of the genus Brevibacterium or Corynebacterium and having been inserted therein a restriction endonuclease fragment of chromosomal DNA controlling α-amino-β-hydroxy valeric acid resistance derived from a DNA-donor strain of the genus Brevibacterium or Corynebacterium which is resistant to α-amino-β-hydroxy valeric acid, and recovering L-threonine accumulated in the resulted culture liquid.

2. The method of claim 1, wherein said recipient strain belongs to *Brevibacterium lactofermentum* or *Corynebacterium glutamicum*.

3. The method of claim 1, wherein said DNA-donor strain belongs to *Brevibacterium lactofermentum* or *Corynebacterium glutamicum*.

4. The method of claim 1, wherein said DNA-donor strain is resistant to an amount of α-amino-β-hydroxy-valeric acid or more than 100 μg/ml.

5. The method of claim 1, wherein said L-threonine producing microooganism is *Corynebacterium glutamicum* FERM-P5973=FERM-BP119 or *Brevibacterium lactofermentum* FERM-P5974=FERM-BP119.

6. A method for constructing an L-threonine producing strain which comprises:
   (a) separating a plasmid DNA from a microorganism of the genus Brevibacterium and Corynebacterium,
   (b) inserting into the plasmid DNA a restriction endonuclease fragment of chromosomal DNA controlling α-amino-β-hydroxy valeric acid resistance derived from a DNA-donor strain of the genus Brevibacterium or Corynebacterium resistant to α-amino-β-hydroxy valeric acid to obtain a recombinant plasmid DNA
   (c) incorporating the recombinant plasmid DNA into a recipient strain of the genus Brevibacterium or Corynebacterium which is sensitive to α-amino-β-hydroxy valeric acid, and
   (d) isolating a strain transformed to become resistant to α-amino-β-hydroxy-valeric acid.

7. The method of claim 6, wherein said recipient strain belongs to *Brevibacterium lactofermentum* or *Corynebacterium glutamicum*

8. The method of claim 6, wherein said DNA-donor strain belongs to *Brevibacterium lactofermentum* or *Corynebacterium glutamicum*.

9. The method of claim 6, wherein said DNA-donor strain is resistant to an amount of L-threonine of more than 1000 μg/ml.

10. The method of claim 6, wherein said L-threonine producing microorganism is *Corynebacterium glutamicum* FERM-P5973=FERM-BP118 or *Brevibacterium lactofermentum* FERM-P5974=FERM-BP119.

* * * * *